(12) United States Patent
Sauer (10) Patent No.: US 11,402,665 B2
(45) Date of Patent: Aug. 2, 2022

(54) OPTICAL ATTACHMENT FOR SURGICAL LOUPE GLASSES

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 390 days.

(21) Appl. No.: 16/568,430

(22) Filed: Sep. 12, 2019

(65) Prior Publication Data

US 2020/0117025 A1 Apr. 16, 2020

Related U.S. Application Data

(60) Provisional application No. 62/745,944, filed on Oct. 15, 2018.

(51) Int. Cl.
*G02C 7/08* (2006.01)
*A61B 90/20* (2016.01)

(52) U.S. Cl.
CPC .............. *G02C 7/088* (2013.01); *A61B 90/20* (2016.02); *G02C 7/086* (2013.01)

(58) Field of Classification Search
CPC .......... G02C 7/088; G02C 7/086; G02C 9/00; G02C 7/10; G02C 7/12; G02B 25/004; G02B 25/007; G02B 30/25; A61B 90/20; A61B 2090/3616; A61B 2090/502
See application file for complete search history.

(56) References Cited

U.S. PATENT DOCUMENTS

2010/0053311 A1\* 3/2010 Luber .................. G02B 25/004
  348/53
2019/0384065 A1\* 12/2019 Shau .................... H04N 5/2253

FOREIGN PATENT DOCUMENTS

WO  2016142263  9/2016
WO  WO-2016142263 A1 \* 9/2016 ............. G02C 7/104

OTHER PUBLICATIONS

Jan. 1, 2020 Website; Ease-In-Shields Laser Protection Inserts, https://www.orascoptic.com/products/laser-protection/ease-in-shields.

\* cited by examiner

*Primary Examiner* — Mustak Choudhury
(74) *Attorney, Agent, or Firm* — Michael E. Coyne (57) ABSTRACT

An optical attachment for surgical loupe glasses is disclosed. The optical attachment for surgical loupe glasses includes a visor sized to cover at least a portion of a first carrier lens of the surgical loupe glasses. The optical attachment also includes at least one loupe orienting feature defined by the visor.

12 Claims, 10 Drawing Sheets

OPTICAL ATTACHMENT FOR SURGICAL LOUPE GLASSES

REFERENCE TO RELATED APPLICATION

This Patent Application claims priority to U.S. Provisional Patent Application No. 62/745,944 filed Oct. 15, 2018 and entitled "OPTICAL ATTACHMENT FOR SURGICAL LOUPE GLASSES." The Ser. No. 62/745,944 application is hereby incorporated by reference in its entirety.

FIELD

The claimed invention relates to optical attachments, and more specifically to optical attachments for surgical loupe glasses.

BACKGROUND

Figure 1:
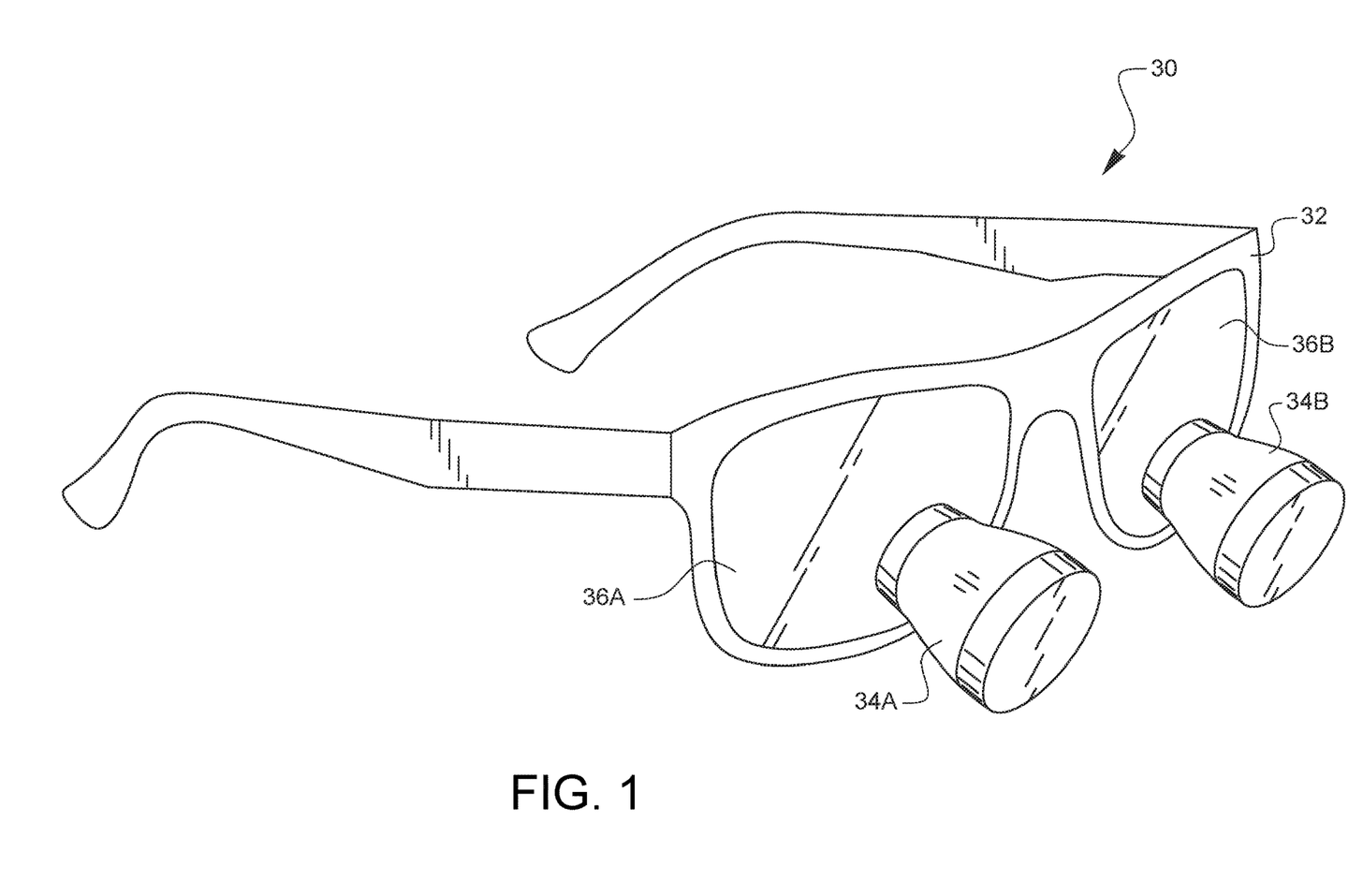
FIG. 1 is a top-right-front perspective view of one typical embodiment of surgical loupe glasses.

Modern advances in cardiac surgery have made it possible to replace heart valves using minimally invasive surgical techniques. As minimally invasive techniques have improved, surgeons have been able to operate on patients through smaller and smaller access holes, resulting in less perioperative pain and shorter recovery times. Surgeons will often wear surgical loupe glasses to help them see better during an operation. For example, FIG. 1 illustrates one typical embodiment of surgical loupe glasses 30. The glasses 30 have a frame 32 which hold right and left carrier lenses 36A, 36B, respectively. Each carrier lens 36A, 36B holds (or carries) an optical loupe 34A, 34B, respectively. The optical loupes 34A, 34B have magnifying lenses which the surgeon can look through for an enlarged view and more detail of the surgical site. For each pair of glasses 30, the optical loupes 34A, 34B are custom located to correspond to a particular surgeon's eye spacing so that the surgeon may focus properly on the enlarged image when directing his/her gaze through the optical loupes. The carrier lenses 36A, 36B may be non-prescription or prescription lenses, depending on the needs of the surgeon in question. Such surgical loupe glasses 30 are expensive and custom tailored to each given surgeon.

As incisions for minimally invasive surgery have gotten smaller, it has become more difficult for surgeons to see target surgical areas through the small incisions, even when wearing their loupe glasses. As a result, endoscopes have become one of the enabling technologies for minimally invasive surgery. Endoscopes are small optical systems which can be coupled to cameras, and which are able to provide a view of the surgical site. Unfortunately, typical endoscopes only capture a two-dimensional (2D) image, which means that surgeons may struggle with depth perception when attempting to perform minimally invasive surgery while observing the surgical site on a 2D monitor.

Recently, however, endoscope manufacturers have been developing three-dimensional (3D) endoscopes to help address this problem. Such scopes have two lens systems and corresponding cameras to capture the 3D image. The images are displayed on special monitors which are able to display two different channels of image information: a left image and a right image. This can be done in a variety of ways known to those skilled in the art, including by polarizing each set of visual information differently. In such a situation, the user would wear special glasses with different polarizing lenses in each side of the frame. A first type of polarizing lens would allow only one visual channel to pass to the left eye for viewing, while a second type of polarizing lens would allow only the other visual channel to pass to the right eye for viewing. The human brain interprets the two different images captured by the 3D endoscope as a 3D image, providing surgeons with a greatly needed depth perception when using endoscopes for minimally invasive surgery.

Unfortunately, it is still desirable for surgeons to be able to use loupes for some portions of their surgeries, even minimally invasive surgeries. While a surgeon could have a special pair of surgical loupe glasses made up with specially polarized carrier lenses, they would still need a different pair of glasses for non-polarized (non-3D) use. Furthermore, it is very expensive to have multiple surgical loupe glasses made up, and such a solution would be exacerbated by the presence of many differing 3D technologies, each potentially requiring its own special set of custom surgical loupe glasses. Surgeons are unlikely to support such a solution. In the meantime, surgeons observed working with 3D displays have been swapping between two different sets of glasses: one set for 3D viewing, and a different set for surgical loupes. This is not a simple matter given that surgical gloves need to be removed each time when the surgeon wants to change glasses.

Therefore, it would be desirable to have an inexpensive optical attachment for surgical loupe glasses which would enable surgeons to convert their surgical loupe glasses to be compatible with 3D display technologies while still enabling loupe usage as desired, and which can accommodate a wide variety of optical eye spacings.

SUMMARY

An optical attachment for surgical loupe glasses is disclosed. The optical attachment for surgical loupe glasses includes a visor sized to cover at least a portion of a first carrier lens of the surgical loupe glasses. The optical attachment also includes at least one loupe orienting feature defined by the visor.

Another optical attachment for surgical loupe glasses is disclosed. The optical attachment for surgical loupe glasses includes a first visor sized to cover at least a portion of a first carrier lens of the surgical loupe glasses, a second visor sized to cover at least a portion of a second carrier lens of the surgical loupe glasses, a coupler between the first and second visor, a first loupe orienting feature defined by the visor, and a second loupe orienting feature defined by the visor.

DETAILED DESCRIPTION

Figure 2A:
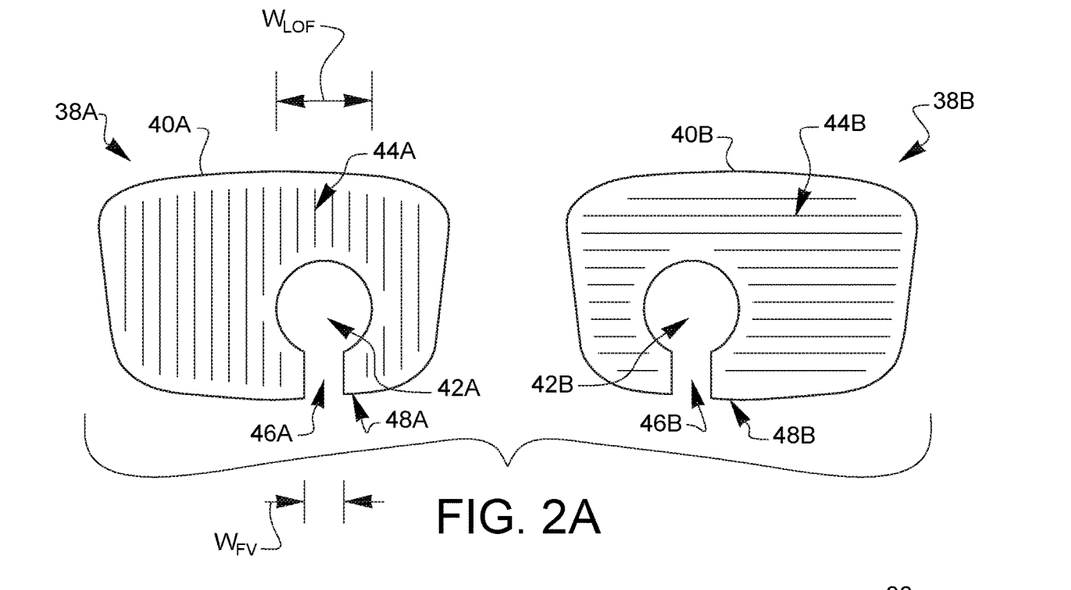
FIG. 2A is a front view of one embodiment of optical attachments for surgical loupe glasses.

FIG. 2A illustrates one embodiment of optical attachments 38A, 38B for surgical loupe glasses. The first optical attachment 38A has a visor 40A which is sized to cover at least a portion of a first carrier lens of a pair of surgical loupe glasses, such as the surgical loupe glasses 30 of FIG. 1. The first optical attachment 38A also has at least one loupe orienting feature 42A defined by the visor 40A. In this embodiment, the loupe orienting feature 42A has an arcuate shape which is sized to correspond to the shape of the loupe 34A where it contacts a carrier lens 36A of a pair of surgical loupe glasses 30. The visor 40A has a light filter 44A. Depending on the embodiment, the light filter 44A could include one or more of a variety of different light filters, including, but not limited to a polarization filter and a color filter. In the example embodiment of FIG. 2A, the light filter 44A is a vertical polarization filter illustrated schematically with the vertical shading lines. In other embodiments, the visor 30A could be opaque. The visor 40A further defines a flex void 46A in communication between the loupe orienting feature 42A and an outer edge 48A of the visor 40A. In this embodiment, the width $W_{FV}$ of the flex void 46A is smaller than a width $W_{LOF}$ of the loupe orienting feature. In some embodiments, as will be shown below with regard to FIG. 9. the flex void 46A does not need to reach the edge.

Similarly, the second optical attachment 38B has a visor 40B which is sized to cover at least a portion of a first carrier lens of a pair of surgical loupe glasses, such as the surgical loupe glasses 30 of FIG. 1. The second optical attachment 38B also has at least one loupe orienting feature 42B defined by the visor 40B. In this embodiment, the loupe orienting feature 42B has an arcuate shape which is sized to correspond to the shape of the loupe 34B where it contacts a carrier lens 36B of a pair of surgical loupe glasses 30. The visor 40B has a light filter 44B. Depending on the embodi-ment, the light filter 44B could include one or more of a variety of different light filters, including, but not limited to a polarization filter and a color filter. In the example embodiment of FIG. 2B, the light filter 44B is a horizontal polarization filter illustrated schematically with the horizontal shading lines. In other embodiments, the visor 30B could be opaque. The visor 40B further defines a flex void 46B in communication between the loupe orienting feature 42B and an outer edge 48B of the visor 40B. In some embodiments, as will be shown below with regard to FIG. 9. the flex void 46B does not need to reach the edge.

Figure 2B:
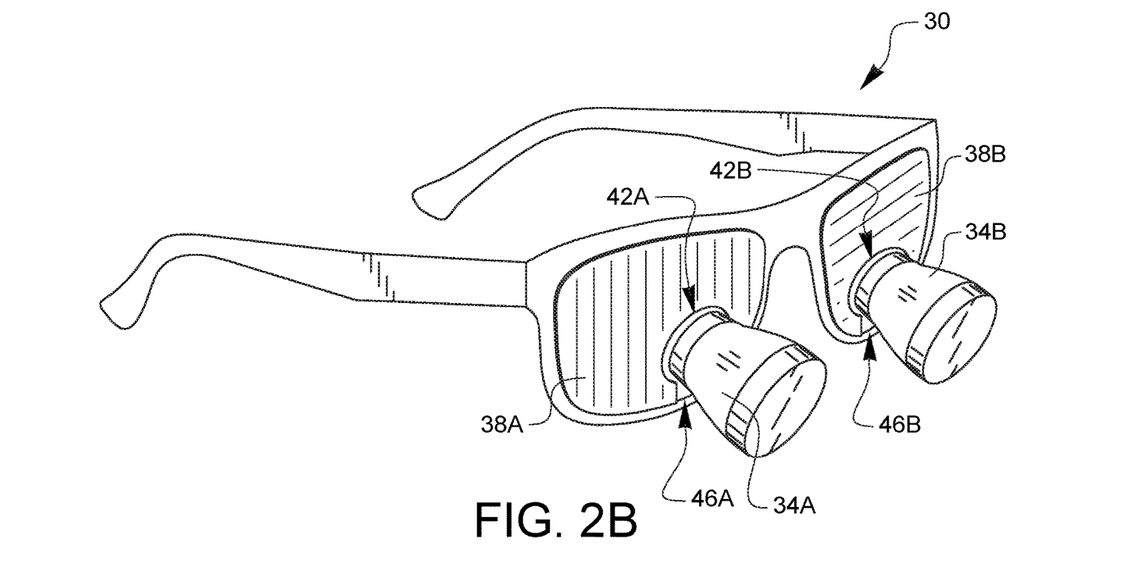
FIG. 2B is a top-right-front perspective view of the optical attachments of FIG. 2A installed on a pair of surgical loupe glasses.

FIG. 2B is a perspective view of the optical attachments 38A, 38B of FIG. 2A installed on a pair of surgical loupe glasses 30. The flex voids 46A, 46B have allowed the loupe orienting features 42A, 42B to be aligned over respective loupes 34A, 34B, thereby converting the carrier lens portions of the surgical loupe glasses for 3D viewing of a 3D display (by virtue of the differing light filters 44A, 44B on each of the optical attachments 38A, 38B), while still allowing the surgeon to have magnified vision when looking through the loupes 34A, 34B. This can be set up before a surgical procedure using the surgeon's regular or prescription surgical loupe glasses, does not require permanent modification to the surgical loupe glasses, and is easily removable for other surgical procedures.

Figure 3A:
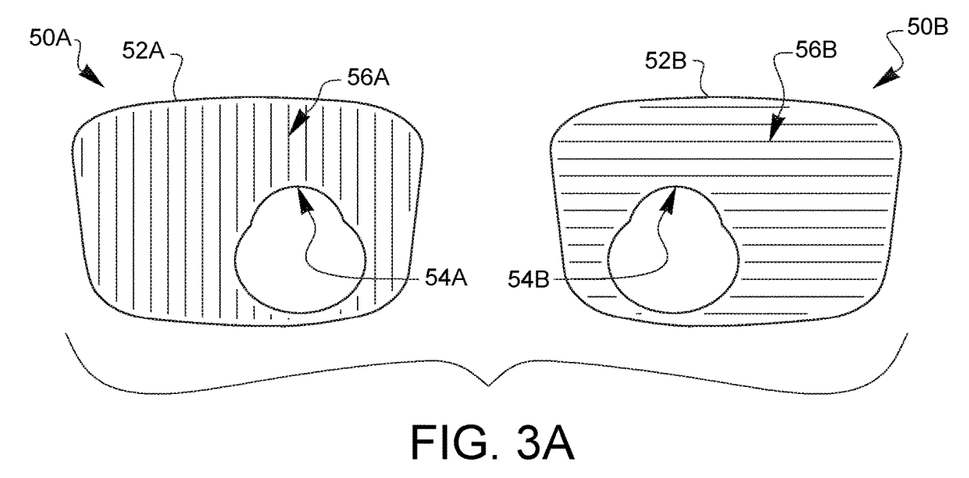
FIG. 3A is a front view of another embodiment of optical attachments for surgical loupe glasses.

FIG. 3A illustrates another embodiment of optical attachments 50A, 50B for surgical loupe glasses. The first optical attachment 50A has a visor 52A which is sized to cover at least a portion of a first carrier lens of a pair of surgical loupe glasses, such as the surgical loupe glasses 30 of FIG. 1. The first optical attachment 50A also has at least one loupe orienting feature 54A defined by the visor 52A. In this embodiment, the loupe orienting feature 54A has an arcuate shape which is sized to correspond to the shape of the loupe 34A where it contacts a carrier lens 36A of a pair of surgical loupe glasses 30. Furthermore, in this embodiment, the loupe orienting feature 54A is completely contained within the visor 52A. The visor 52A has a light filter 56A. Depending on the embodiment, the light filter 56A could include one or more of a variety of different light filters, including, but not limited to a polarization filter and a color filter. In the example embodiment of FIG. 3A, the light filter 56A is a vertical polarization filter illustrated schematically with the vertical shading lines. In other embodiments, the visor 52A could be opaque.

Similarly, the second optical attachment 50B has a visor 52B which is sized to cover at least a portion of a second carrier lens of a pair of surgical loupe glasses, such as the surgical loupe glasses 30 of FIG. 1. The second optical attachment 50B also has at least one loupe orienting feature 54B defined by the visor 52B. In this embodiment, the loupe orienting feature 54B has an arcuate shape which is sized to correspond to the shape of the loupe 34B where it contacts a carrier lens 36B of a pair of surgical loupe glasses 30. Furthermore, in this embodiment, the loupe orienting feature 54B is completely contained within the visor 52B. The visor 52B has a light filter 56B. Depending on the embodiment, the light filter 56B could include one or more of a variety of different light filters, including, but not limited to a polarization filter and a color filter. In the example embodiment of FIG. 3B, the light filter 56B is a vertical polarization filter illustrated schematically with the vertical shading lines. In other embodiments, the visor 52B could be opaque.

Figure 3B:
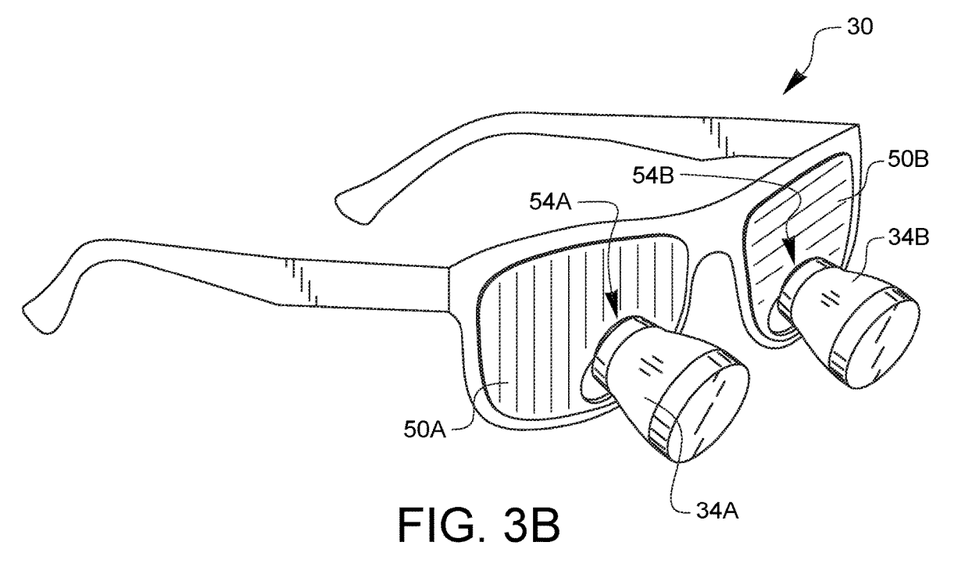
FIG. 3B is a top-right-front perspective view of the optical attachments of FIG. 3A installed on a pair of surgical loupe glasses.

FIG. 3B is a perspective view of the optical attachments 50A, 50B of FIG. 3A installed on a pair of surgical loupe glasses 30. The loupe orienting features 54A, 54B have been aligned over respective loupes 34A, 34B, thereby converting the carrier lens portions of the surgical loupe glasses for 3D viewing of a 3D display (by virtue of the differing light filters 56A, 56B on each of the optical attachments 50A, 50B), while still allowing the surgeon to have magnified vision when looking through the loupes 34A, 34B. This can be set up before a surgical procedure using the surgeon's regular or prescription surgical loupe glasses, does not require permanent modification to the surgical loupe glasses, and is easily removable for other surgical procedures.

Figure 4A:
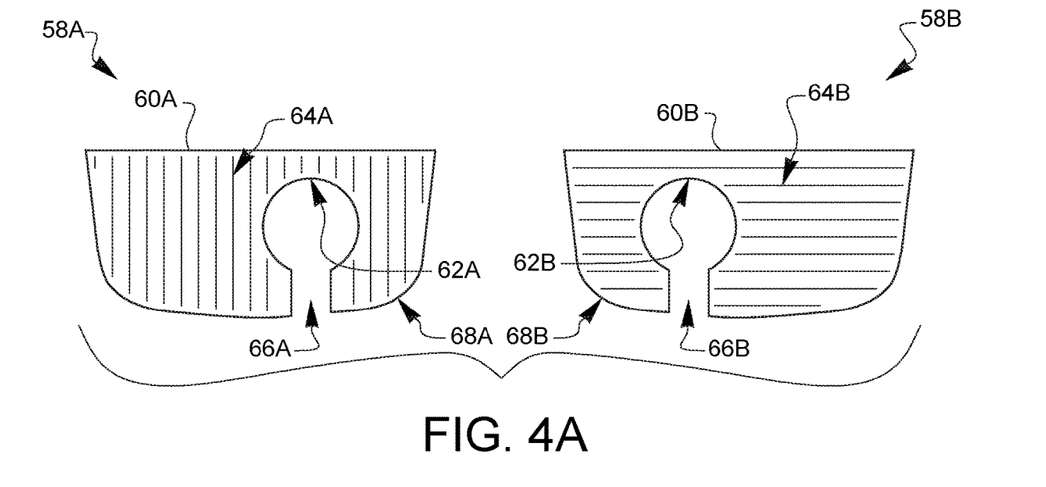
FIG. 4A is a front view of another embodiment of optical attachments for surgical loupe glasses.

FIG. 4A illustrates another embodiment of optical attachments 58A, 58B for surgical loupe glasses. The first optical attachment 58A has a visor 60A which is sized to cover only a portion of a first carrier lens of a pair of surgical loupe glasses, such as the surgical loupe glasses 30 of FIG. 1. The first optical attachment 58A also has at least one loupe orienting feature 62A defined by the visor 60A. In this embodiment, the loupe orienting feature 62A has an arcuate shape which is sized to correspond to the shape of the loupe 34A where it contacts a carrier lens 36A of a pair of surgical loupe glasses 30. The visor 60A has a light filter 64A. Depending on the embodiment, the light filter 64A could include one or more of a variety of different light filters, including, but not limited to a polarization filter and a color filter. In the example embodiment of FIG. 4A, the light filter 64A is a vertical polarization filter illustrated schematically with the vertical shading lines. In other embodiments, the visor 60A could be opaque. The visor 60A further defines a flex void 66A in communication between the loupe orienting feature 62A and an outer edge 68A of the visor 60A.

Similarly, the second optical attachment 58B has a visor 60B which is sized to cover only a portion of a first carrier lens of a pair of surgical loupe glasses, such as the surgical loupe glasses 30 of FIG. 1. The second optical attachment 58B also has at least one loupe orienting feature 62B defined by the visor 60B. In this embodiment, the loupe orienting feature 62B has an arcuate shape which is sized to correspond to the shape of the loupe 34B where it contacts a carrier lens 36B of a pair of surgical loupe glasses 30. The visor 60B has a light filter 64B. Depending on the embodiment, the light filter 64B could include one or more of a variety of different light filters, including, but not limited to a polarization filter and a color filter. In the example embodiment of FIG. 4A, the light filter 64B is a horizontal polarization filter illustrated schematically with the horizontal shading lines. In other embodiments, the visor 60B could be opaque. The visor 60B further defines a flex void 66B in communication between the loupe orienting feature 62B and an outer edge 68B of the visor 60B.

Figure 4B:
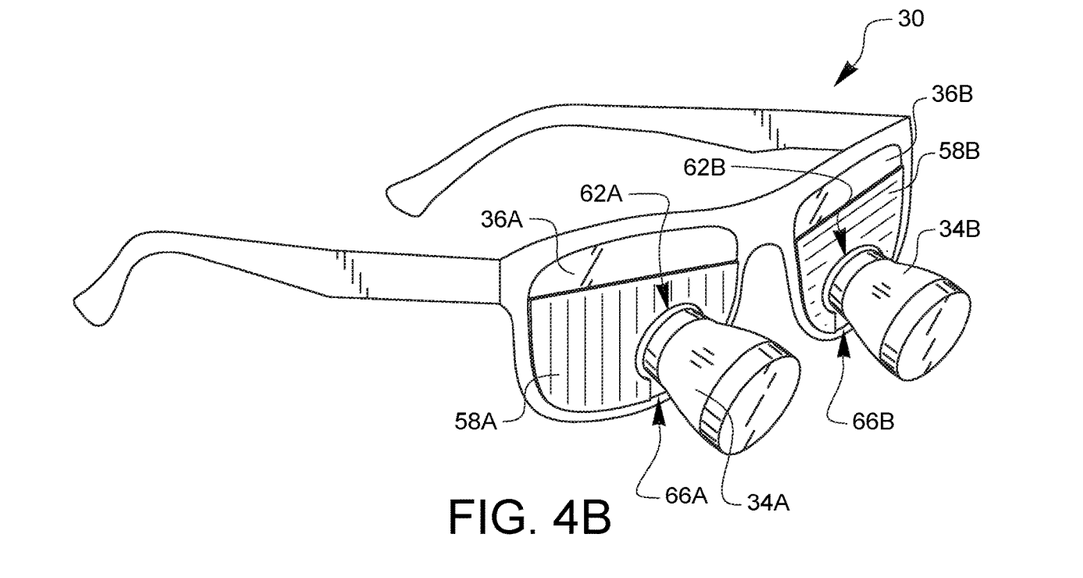
FIG. 4B is a top-right-front perspective view of the optical attachments of FIG. 4A installed on a pair of surgical loupe glasses.

FIG. 4B is a perspective view of the optical attachments 58A, 58B of FIG. 4A installed on a pair of surgical loupe glasses 30. The flex voids 66A, 66B have allowed the loupe orienting features 62A, 62B to be aligned over respective loupes 34A, 34B, thereby converting a portion of the carrier lens portions 36A, 36B of the surgical loupe glasses for 3D viewing of a 3D display (by virtue of the differing light filters 64A, 64B on each of the optical attachments 58A, 58B), while still allowing the surgeon to have magnified vision when looking through the loupes 34A, 34B. Since the attachments 58A, 58B in this embodiment do not fully cover the carrier lenses 36A, 36B, the surgeon can also have a portion of the carrier lenses 36A, 36B which can be looked through without having to look through the filters of the attachments. Such embodiments enable magnified vision through the loupes, enable 3D vision through the optical attachments, and enable standard vision through the carrier lenses, all without needing to swap glasses, remove gloves, or otherwise inconvenience the surgeon. As with previous embodiments, this can be set up before a surgical procedure using the surgeon's regular or prescription surgical loupe glasses, does not require permanent modification to the surgical loupe glasses, and is easily removable for other surgical procedures.

Figure 5A:
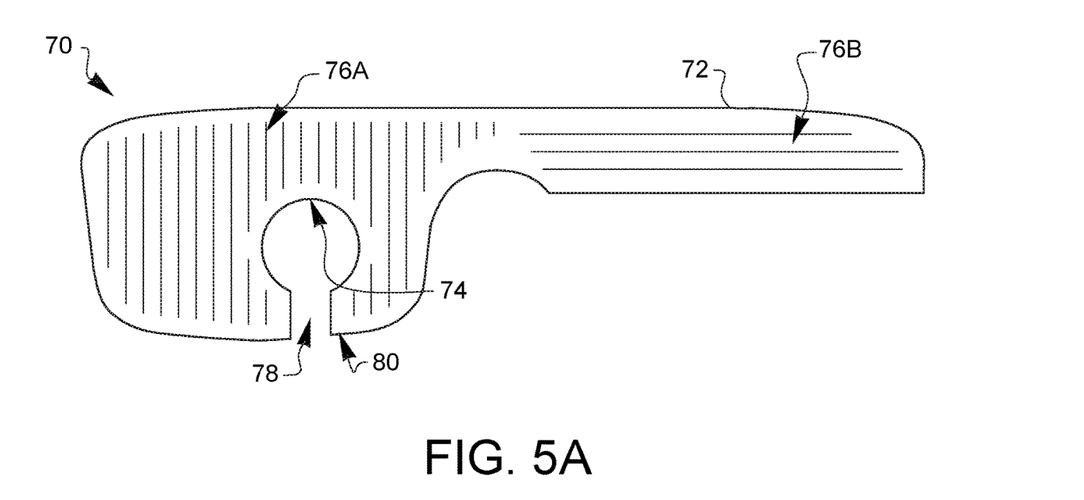
FIG. 5A is a front view of another embodiment of an optical attachment for surgical loupe glasses.

FIG. 5A illustrates another embodiment of an optical attachment 70 for surgical loupe glasses. The optical attachment 70 has a visor 72 which is sized to cover at least a portion of two carrier lenses of a pair of surgical loupe glasses, such as the surgical loupe glasses 30 of FIG. 1. The optical attachment 70 also has a loupe orienting feature 74 defined by the visor 72. In this embodiment, the loupe orienting feature 74 has an arcuate shape which is sized to correspond to the shape of the loupe 34A where it contacts a carrier lens 36A of a pair of surgical loupe glasses 30. In other embodiments, the loupe orienting feature 74 may have other shapes, and possibly different shapes to correspond to loupes having an outer housing which is not arcuate. Such shapes may be useful for orienting the optical attachment 70. The visor 72 has a first light filter 76A and a second light filter 76B. Depending on the embodiment, the light filters 76A, 76B could include one or more of a variety of different light filters, including, but not limited to a polarization filter and a color filter. In the example embodiment of FIG. 5A, the first light filter 76A is a vertical polarization filter illustrated schematically with the vertical shading lines, while the second light filter 76B is a horizontal polarization filter illustrated schematically with the horizontal shading lines. In other embodiments, the visor 72 could be opaque. The visor 72 further defines a flex void 78 in communication between the loupe orienting feature 74 and an outer edge 80 of the visor 72.

Figure 5B:
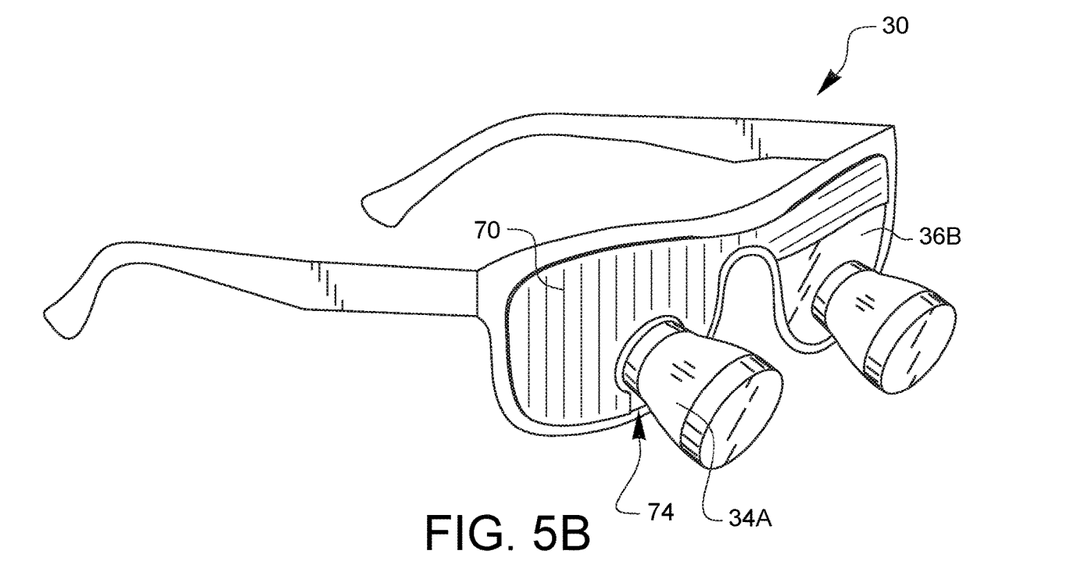
FIG. 5B is a top-right-front perspective view of the optical attachment of FIG. 5A installed on a pair of surgical loupe glasses.

FIG. 5B is a perspective view of the optical attachment 70 of FIG. 5A installed on a pair of surgical loupe glasses 30. The flex void 78 has allowed the loupe orienting feature 74 to be aligned over the loupe 34A, thereby converting the carrier lens portions of the surgical loupe glasses for 3D viewing of a 3D display (by virtue of the differing light filters 76A, 76B on the optical attachment 70), while still allowing the surgeon to have magnified vision when looking through the loupes 34A, 34B. In this embodiment, a portion of the second carrier lens 36B is still uncovered and could be used for non-3D and non-magnified vision. This can be set up before a surgical procedure using the surgeon's regular or prescription surgical loupe glasses, does not require permanent modification to the surgical loupe glasses, and is easily removable for other surgical procedures. Furthermore, since the optical attachment 70 only couples to a single loupe 34A, it can work with a variety of glasses having different spacings between loupes 34A, 34B.

Figure 6A:
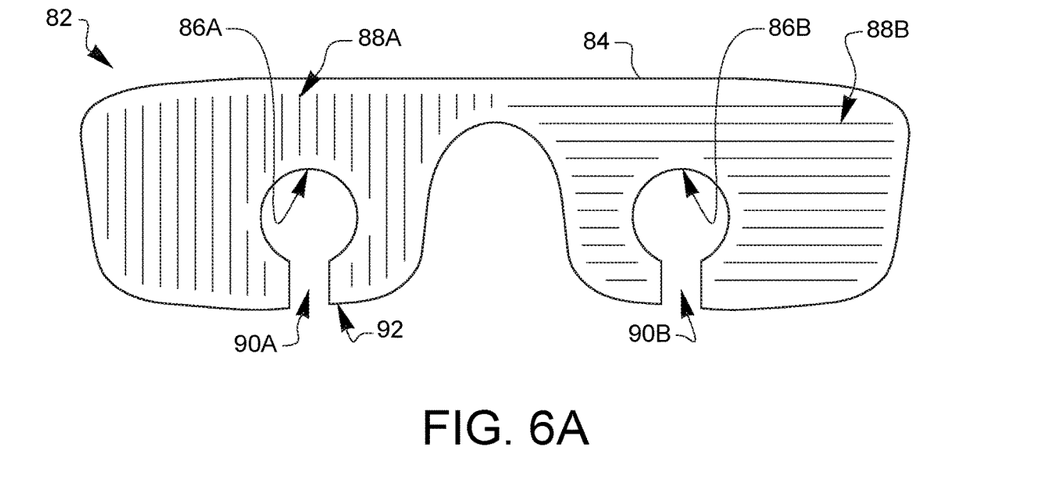
FIG. 6A is a front view of another embodiment of an optical attachment for surgical loupe glasses.

FIG. 6A illustrates another embodiment of an optical attachment 82 for surgical loupe glasses. The optical attachment 82 has a visor 84 which is sized to cover at least a portion of two carrier lenses of a pair of surgical loupe glasses, such as the surgical loupe glasses 30 of FIG. 1. The optical attachment 82 also has first and second loupe orienting features 86A, 86B defined by the visor 84. In this embodiment, the two loupe orienting features 86A, 86B have an arcuate shape which is sized to correspond to the shape of the loupes 34A, 34B where they contact the carrier lenses 36A, 36B, respectively, of a pair of surgical loupe glasses 30. The visor 84 has a first light filter 88A and a second light filter 88B. Depending on the embodiment, the light filters 88A, 88B could include one or more of a variety of different light filters, including, but not limited to a polarization filter and a color filter. In the example embodiment of FIG. 6A, the first light filter 88A is a vertical polarization filter illustrated schematically with the vertical shading lines, while the second light filter 88B is a horizontal polarization filter illustrated schematically with the horizontal shading lines. In other embodiments, the visor 84 could be opaque. The visor 84 further defines a first flex void 90A in communication between the first loupe orienting feature 86A and an outer edge 92 of the visor 84. The visor 84 also defines a second flex void 90B in communication between the second loupe orienting feature 86B and the outer edge 92 of the visor 84.

Figure 6B:
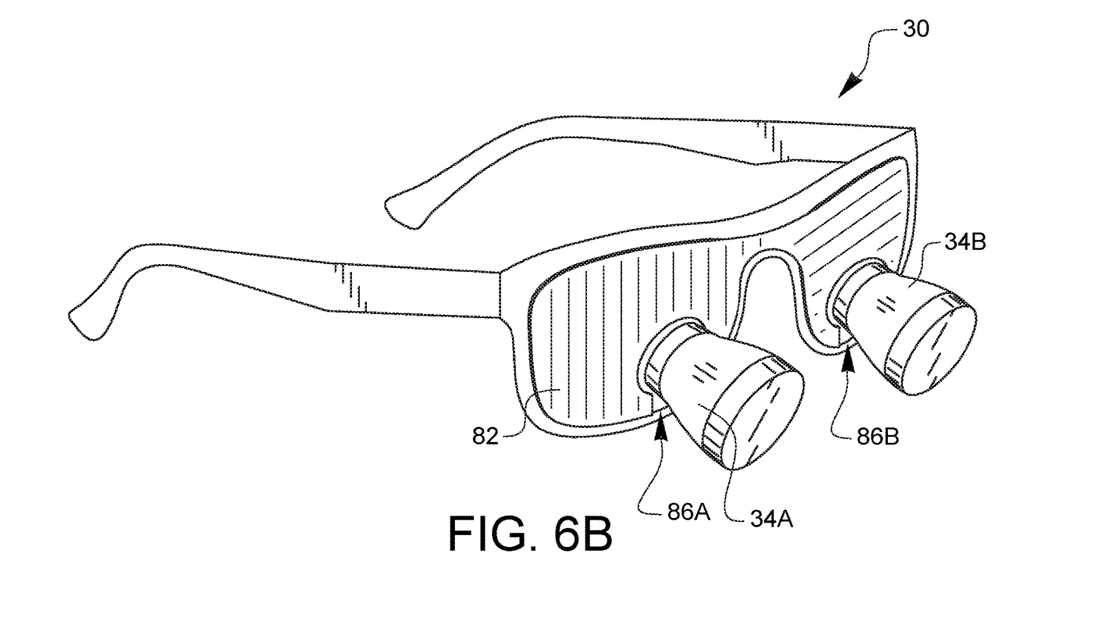
FIG. 6B is a top-right-front perspective view of the optical attachment of FIG. 6A installed on a pair of surgical loupe glasses.

FIG. 6B is a perspective view of the optical attachment 82 of FIG. 6A installed on a pair of surgical loupe glasses 30. The first and second flex voids 90A, 90B have allowed the loupe orienting features 86A, 86B to be aligned over the respective loupes 34A, 34B, thereby converting the carrier lens portions of the surgical loupe glasses for 3D viewing of a 3D display (by virtue of the differing light filters 88A, 88B on the optical attachment 82), while still allowing the surgeon to have magnified vision when looking through the loupes 34A, 34B. This can be set up before a surgical procedure using the surgeon's regular or prescription surgical loupe glasses, does not require permanent modification to the surgical loupe glasses, and is easily removable for other surgical procedures.

Figure 7A:
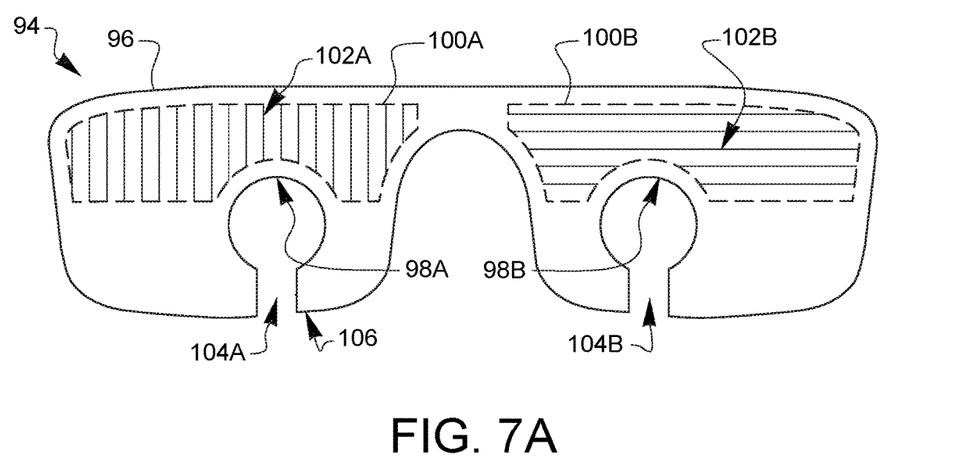
FIG. 7A is a front view of another embodiment of an optical attachment for surgical loupe glasses.

FIG. 7A illustrates another embodiment of an optical attachment 94 for surgical loupe glasses. The optical attachment 94 has a visor 96 which is sized to cover at least a portion of two carrier lenses of a pair of surgical loupe glasses, such as the surgical loupe glasses 30 of FIG. 1. The optical attachment 94 also has first and second loupe orienting features 98A, 98B defined by the visor 96. In this embodiment, the loupe orienting features 98A, 98B have an arcuate shape which is sized to correspond to the shape of the loupes 34A, 34B where they contact the carrier lenses 36A, 36B, respectively, of a pair of surgical loupe glasses 30. The visor 96 has a first optical region 100A and a second optical region 100B. The first optical region 100A is positioned to overlap with at least a portion of a first carrier lens, while the second optical region 100B is positioned to overlap with at least a portion of a second carrier lens. In this embodiment the first optical region 100A has a first light filter 102A, while the second optical region 100B has a second light filter 102B. Depending on the embodiment, the light filters 102A, 102BB could include one or more of a variety of different light filters, including, but not limited to a polarization filter and a color filter. In the example embodiment of FIG. 7A, the first light filter 102A is a vertical polarization filter illustrated schematically with the vertical shading lines, while the second light filter 102B is a horizontal polarization filter illustrated schematically with the horizontal shading lines. In other embodiments, the visor 96 could be opaque. The optical regions 100A, 100B provide filtering functionality, for example to support 3D viewing, while the visor 96 portions outside of the optical regions can be of different properties (for example, transparent), thereby allowing other types of vision. The visor 96 further defines a first flex void 104A in communication between the first loupe orienting feature 98A and an outer edge 106 of the visor 96. The visor 96 also defines a second flex void 104B in communication between the second loupe orienting feature 98B and the outer edge 106 of the visor 96.

Figure 7B:
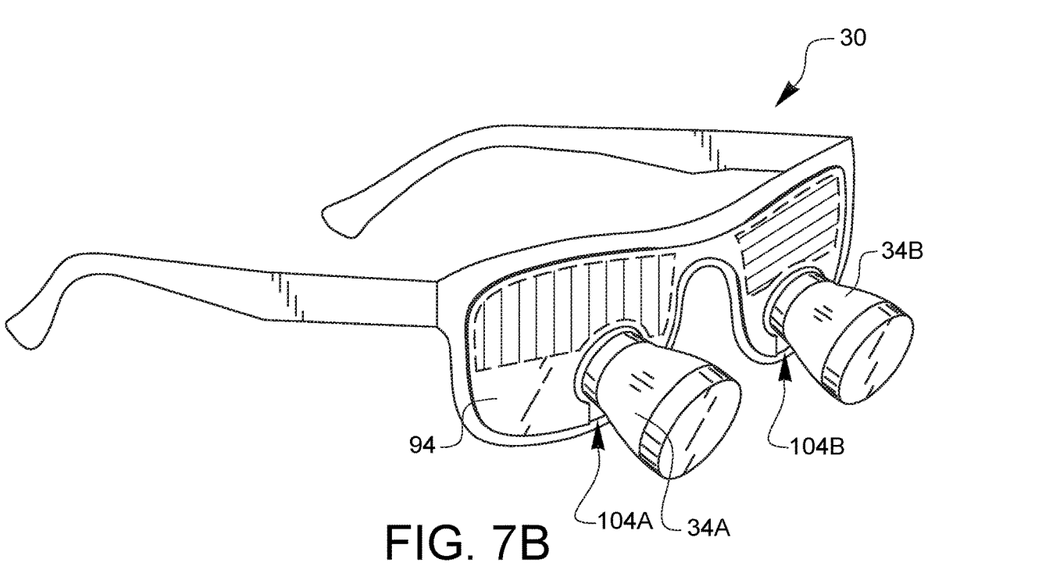
FIG. 7B is a top-right-front perspective view of the optical attachment of FIG. 7A installed on a pair of surgical loupe glasses.

FIG. 7B is a perspective view of the optical attachment 94 of FIG. 7A installed on a pair of surgical loupe glasses 30. The first and second flex voids 104A, 104B have allowed the loupe orienting features 98A, 98B to be aligned over the respective loupes 34A, 34B, thereby converting the carrier lens portions of the surgical loupe glasses for 3D viewing of a 3D display (by virtue of the differing light filters 102A, 102B on the optical attachment 94), while still allowing the surgeon to have magnified vision when looking through the loupes 34A, 34B. This can be set up before a surgical procedure using the surgeon's regular or prescription surgical loupe glasses, does not require permanent modification to the surgical loupe glasses, and is easily removable for other surgical procedures.

Figure 8:
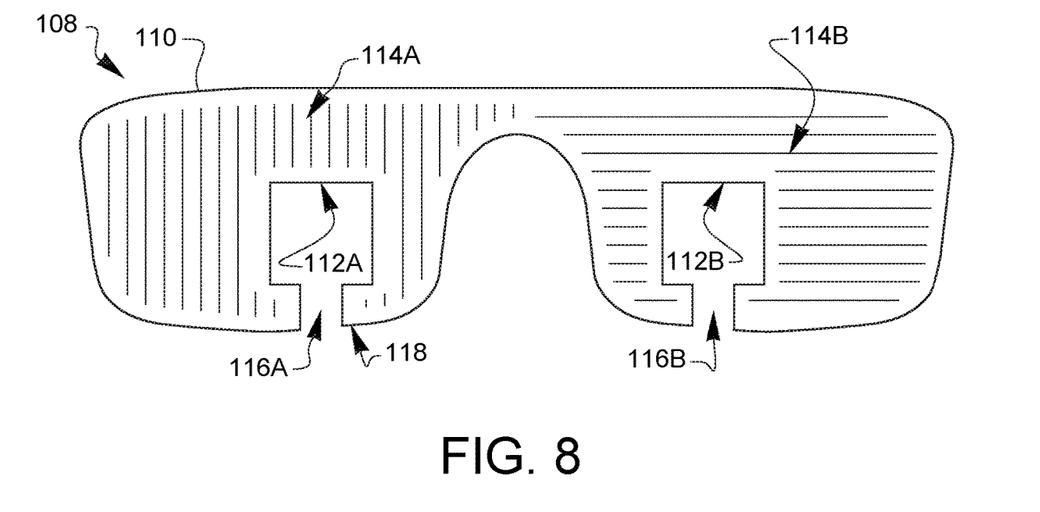
FIG. 8 is a front view of another embodiment of an optical attachment for surgical loupe glasses.

FIG. 8 illustrates another embodiment of an optical attachment 108 for surgical loupe glasses. The optical attachment 108 has a visor 110 which is sized to cover at least a portion of two carrier lenses of a pair of surgical loupe glasses, such as the surgical loupe glasses 30 of FIG. 1. The optical attachment 108 also has first and second loupe orienting features 112A, 112B defined by the visor 110. In this embodiment, the loupe orienting features 112A, 112B have a squared shape. The visor 110 has a first light filter 114A and a second light filter 114B. Depending on the embodiment, the light filters 114A, 114B could include one or more of a variety of different light filters, including, but not limited to a polarization filter and a color filter. In the example embodiment of FIG. 8, the first light filter 114A is a vertical polarization filter illustrated schematically with the vertical shading lines, while the second light filter 114B is a horizontal polarization filter illustrated schematically with the horizontal shading lines. In other embodiments, the visor 110 could be opaque. The visor 110 further defines a first flex void 116A in communication between the first loupe orienting feature 112A and an outer edge 118 of the visor 110. The visor 110 also defines a second flex void 116B in communication between the second loupe orienting feature 112B and the outer edge 118 of the visor 110.

Figure 9:
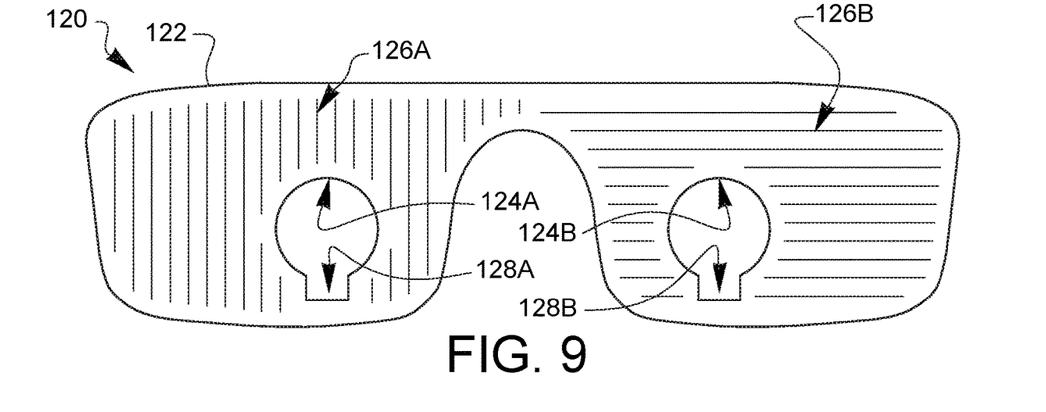
FIG. 9 is a front view of another embodiment of an optical attachment for surgical loupe glasses.

FIG. 9 illustrates another embodiment of an optical attachment 120 for surgical loupe glasses. The optical attachment 120 has a visor 122 which is sized to cover at least a portion of two carrier lenses of a pair of surgical loupe glasses, such as the surgical loupe glasses 30 of FIG. 1. The optical attachment 120 also has first and second loupe orienting features 124A, 124B defined by the visor 122. In this embodiment, the loupe orienting features 124A, 124B have an arcuate shape which is sized to correspond to the shape of the loupes 34A, 34B where they contact the carrier lenses 36A, 36B, respectively, of a pair of surgical loupe glasses 30. The visor 122 has a first light filter 126A and a second light filter 126B. Depending on the embodiment, the light filters 126A, 126B could include one or more of a variety of different light filters, including, but not limited to a polarization filter and a color filter. In the example embodiment of FIG. 9, the first light filter 126A is a vertical polarization filter illustrated schematically with the vertical shading lines, while the second light filter 126B is a horizontal polarization filter illustrated schematically with the horizontal shading lines. In other embodiments, the visor 122 could be opaque. The visor 122 further defines a first flex void 128A in communication with the first loupe orienting feature 124A. The visor 122 also defines a second flex void 128B in communication with the second loupe orienting feature 124B.

Figure 10:
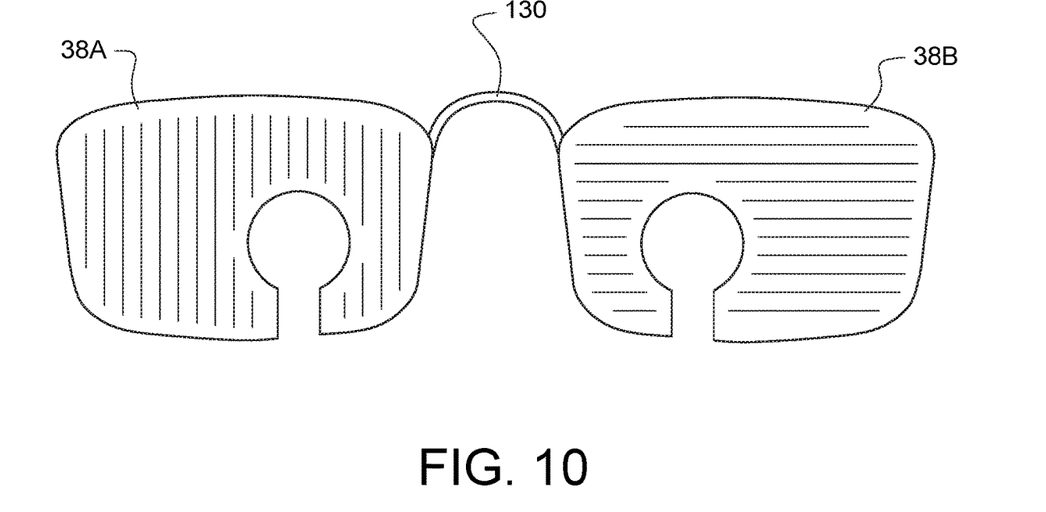
FIG. 10 is a front view of an embodiment where the optical attachments of FIG. 2A are joined by an embodiment of a coupler.

FIG. 10 illustrates an embodiment where the optical attachments 38A, 38B discussed above with regard to FIG. 2A are joined by an embodiment of a coupler 130. Depending on the embodiment, the coupler could be rigid, flexible, shapeable and could be made from a variety of materials. In some embodiments, the coupler 130 could also be configured to couple to the frame of a pair of surgical loupe glasses.

Figure 11:
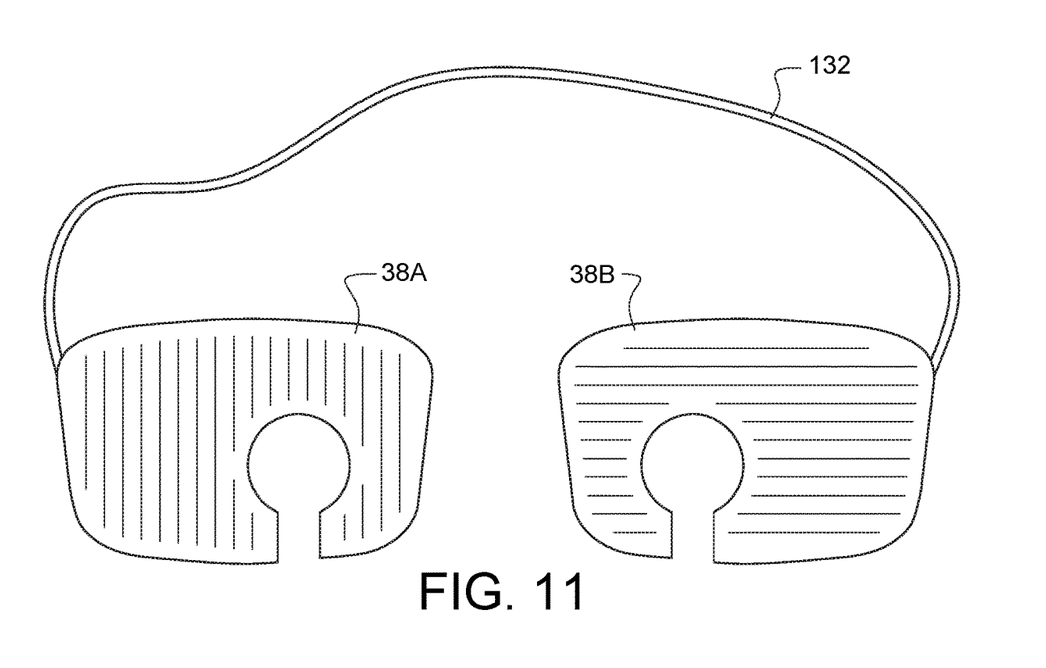
FIG. 11 is a front view of an embodiment where the optical attachments of FIG. 2A are joined by another embodiment of a coupler.

FIG. 11 illustrates another embodiment where the optical attachments 38A, 38B discussed above with regard to FIG. 2A are joined by a further embodiment of a coupler 132. In this embodiment, the coupler 132 is a cord.

Figure 12A:
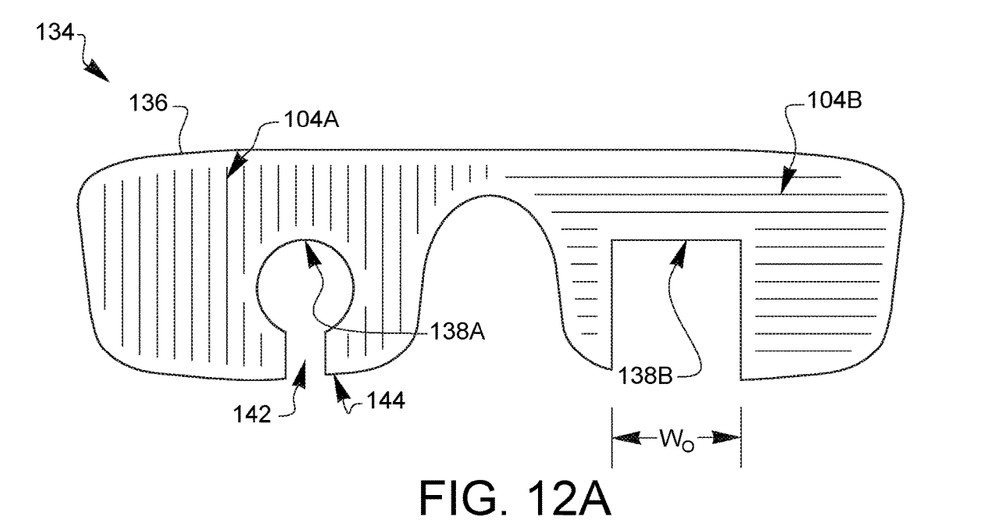
FIG. 12A is a front view of another embodiment of an optical attachment for surgical loupe glasses.

FIG. 12A illustrates another embodiment of an optical attachment 134 for surgical loupe glasses. The optical attachment 134 has a visor 136 which is sized to cover at least a portion of two carrier lenses of a pair of surgical loupe glasses, such as the surgical loupe glasses 30 of FIG. 1. The optical attachment 134 also has first and second loupe orienting features 138A, 138B defined by the visor 136. In this embodiment, the first loupe orienting feature 138A has an arcuate shape which is sized to correspond closely to the shape of the first loupe 34A where it contacts the carrier lens 36A of a pair of surgical loupe glasses 30. The second loupe orienting feature 138B is sized to rest on a top surface of the second loupe 34B, but it has an orientation width WO which is substantially wider than the second loupe 34B. This combination of two different loupe orienting features enables the optical attachment 134 to couple nicely to the first loupe 34A, while being able to accommodate a variety of spacings between the first and second loupes 34A, 34B. As with other embodiments, the visor 136 has a first light filter 140A and a second light filter 140B. Depending on the embodiment, the light filters 140A, 140B could include one or more of a variety of different light filters, including, but not limited to a polarization filter and a color filter. In the example embodiment of FIG. 12A, the first light filter 140A is a vertical polarization filter illustrated schematically with the vertical shading lines, while the second light filter 140B is a horizontal polarization filter illustrated schematically with the horizontal shading lines. In other embodiments, the visor 136 could be opaque. The visor 136 further defines a first flex void 142 in communication between the first loupe orienting feature 138A and an outer edge 144 of the visor 136.

Figure 12B:
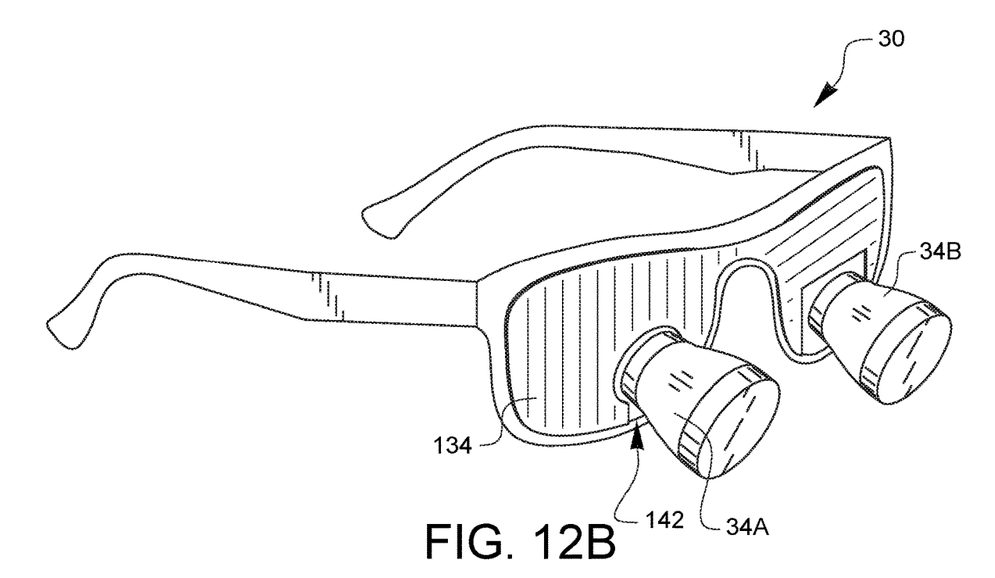
FIG. 12B is a top-right-front perspective view of the optical attachment of FIG. 12A installed on a pair of surgical loupe glasses.

FIG. 12B is a perspective view of the optical attachment 134 of FIG. 12A installed on a pair of surgical loupe glasses 30. The first flex void 142 has allowed the first loupe orienting feature 138A to be aligned over the loupe 34A, while the second loupe orienting feature 138B rests on the second loupe 34B, thereby converting the carrier lens portions of the surgical loupe glasses for 3D viewing of a 3D display (by virtue of the differing light filters 140A, 140B on the optical attachment 134), while still allowing the surgeon to have magnified vision when looking through the loupes 34A, 34B. This can be set up before a surgical procedure using the surgeon's regular or prescription surgical loupe glasses, does not require permanent modification to the surgical loupe glasses, and is easily removable for other surgical procedures.

Various advantages of an optical attachment for surgical loupe glasses have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. An optical attachment assembly configured to be removably secured to a pair of surgical loupe glasses, the pair of surgical loupe glasses comprising a frame that supports a first carrier lens and a second carrier lens, the pair of surgical loupe glasses further comprising a first optical loupe coupled to the first carrier lens and a second optical loupe coupled to the second carrier lens, the optical attachment assembly comprising:
    a first optical attachment comprising:
        a first visor sized to cover at least a first portion of an external surface of the first carrier lens of the pair of surgical loupe glasses, wherein an inner surface of the first visor is in removable contact with the first portion of the external surface of the first carrier lens of the pair of surgical loupe glasses; and
        a first loupe orienting feature defined by one or more first edges formed on the first visor, wherein the one or more first edges of the first loupe orienting feature cooperate to form a segment of a circle that is configured to at least partially surround a bottom portion of the first optical loupe that is disposed at or adjacent to a second portion of the external surface of the first carrier lens of the pair of surgical loupe glasses.

2. The optical attachment assembly of claim 1, wherein the first visor is sized to cover at least the first portion of the external surface of the first carrier lens of the pair of surgical loupe glasses and at least a first portion of an external surface of the second carrier lens of the pair of surgical loupe glasses.

3. The optical attachment assembly of claim 2, further comprising:
    a second loupe orienting feature defined by one or more second edges formed on the first visor, wherein the one or more second edges of the loupe orienting feature cooperate to form a segment of a circle that is configured to at least partially surround a bottom portion the of second optical loupe that is disposed at or adjacent to a second portion of an external surface of the second carrier lens of the pair of surgical loupe glasses.

4. The optical attachment assembly of claim 2, wherein:
    a first portion of the first visor comprises a first polarization filter, wherein the first portion of the first visor overlaps the first portion of the external surface of the first carrier lens; and
    a second portion of the first visor comprises a second polarization filter, wherein the second portion of the first visor overlaps the first portion of the external surface of the second carrier lens.

5. The optical attachment assembly of claim 1, wherein the first visor comprises a light filter.

6. The optical attachment assembly of claim 5, wherein the light filter is selected from the group consisting of a polarization filter and a color filter.

7. The optical attachment assembly of claim 1, wherein the first loupe orienting feature is completely contained within the first visor.

8. The optical attachment assembly of claim 1, wherein the visor further defines a flex void in communication between a first of the at least one loupe orienting feature and an outer edge of the visor.

9. The optical attachment assembly of claim 1, wherein the one or more edges of the first loupe orienting feature include a pair of opposing edges each having a first end portion at a portion of the segment of the circle and a second end portion at a portion of an outer perimeter edge defining the first visor, wherein the pair of opposing edges cooperate to define a first flex void.

10. The optical attachment assembly of claim 9, wherein a width of the first flex void is smaller than a width of the segment of the circle of the first loupe orienting feature.

11. The optical attachment assembly of claim 1, further comprising:
   a second optical attachment comprising:
      a second visor sized to cover at least a first portion of an external surface of the second carrier lens of the pair of surgical loupe glasses, wherein an inner surface of the second visor is in removable contact with the first portion of the external surface of the second carrier lens of the pair of surgical loupe glasses; and
      a second loupe orienting feature defined by one or more second edges formed on the second visor, wherein the one or more second edges of the loupe orienting feature cooperate to form a segment of a circle that is configured to at least partially surround a bottom portion of the second optical loupe that is disposed at or adjacent to a second portion of the external surface of the second carrier lens of the pair of surgical loupe glasses.

12. The optical attachment assembly of claim 11, wherein:
   at least a portion of the first visor comprises a first polarization filter; and
   at least a portion of the second visor comprises a second polarization filter.

\* \* \* \* \*